United States Patent [19]
Otaka et al.

[11] Patent Number: 5,537,037
[45] Date of Patent: Jul. 16, 1996

[54] APPARATUS WITH CANCEL COIL ASSEMBLY FOR CANCELLING A FIELD PARALLEL TO AN AXIAL DIRECTION TO THE PLURAL COILS AND TO A SQUID PICK UP COIL

[75] Inventors: Masahiro Otaka, Hitachi, Japan; Sadato Shimizu, Stanford, Calif.; Kazuo Takaku, Hitachi; Shinji Sakata, Katsuta, both of Japan

[73] Assignee: Hitachi, Ltd., Tokyo, Japan

[21] Appl. No.: 212,927

[22] Filed: Mar. 15, 1994

[30]  Foreign Application Priority Data

Mar. 16, 1993  [JP]  Japan .................................. 5-055516

[51] Int. Cl.⁶ .......................... G01N 27/82; G01N 27/72; G01R 33/02
[52] U.S. Cl. .......................... 324/240; 324/248; 324/225
[58] Field of Search .................................. 324/239, 240, 324/241, 242, 243, 248, 225, 207.52; 505/845, 846

[56]  References Cited

U.S. PATENT DOCUMENTS

| | | | |
|---|---|---|---|
| 4,277,750 | 7/1981 | Bonnet et al. | 324/225 |
| 4,926,127 | 5/1990 | Ausläander et al. | 324/225 |
| 5,004,724 | 4/1991 | De | 324/240 |
| 5,124,648 | 6/1992 | Webb et al. | 324/225 |
| 5,134,368 | 7/1992 | Otaka et al. | 324/240 |
| 5,331,278 | 7/1994 | Evanson et al. | 324/240 |
| 5,367,259 | 11/1994 | Matsumoto et al. | 324/248 |

*Primary Examiner*—Sandra L. O'Shea
*Assistant Examiner*—Roger Phillips
*Attorney, Agent, or Firm*—Antonelli, Terry, Stout & Kraus

[57]  ABSTRACT

A nondestructive inspecting apparatus is arranged to have an exciting magnet for applying an ac magnetic field to a sample and a SQUID for converting change of a magnetic characteristic of the sample occurring when the ac magnetic field is applied to the sample into an electric signal. The exciting magnet is a cancelled coil assembly composed of plural coils having respective polarities.

12 Claims, 9 Drawing Sheets

Y-AXIAL CANCELLED
COIL ASSEMBLY

PLANAR TYPE CANCELLED
COIL ASSEMBLY

APPARATUS WITH CANCEL COIL ASSEMBLY FOR CANCELLING A FIELD PARALLEL TO AN AXIAL DIRECTION TO THE PLURAL COILS AND TO A SQUID PICK UP COIL

BACKGROUND OF THE INVENTION

The present invention relates to a nondestructive inspecting apparatus with a SQUID (Superconducting Quantum Interference Device) and more particularly to the nondestructive inspecting apparatus with a SQUID which is preferable to sensing even a small defect of a sample with high accuracy.

Nuclear Power Plants, in general, are required to nondestructively check structures such as pipes, a pressure vessel or components such as pumps for defects like cracks or the like in the in-service inspection and, if a defect like a crack is found out, to exchange the defective structure or component before it is made more defective. As an apparatus for doing nondestructive inspection, there has been proposed an apparatus with a SQUID in addition to a ultrasonic testing device. The inspecting apparatus with a SQUID has been disclosed in J-P-A-2-78983.

FIG. 8 is a diagram showing a conventional nondestructive inspecting apparatus with a SQUID. In FIG. 8, the nondestructive inspecting apparatus for inspecting a sample 1 for cracks provides a cryostat 2 in which the SQUID itself is held. This cryostat 2 has a flexible pipe 2a connected thereto. The flexible pipe 2a provides a pick-up coil 3 at its tip 2b. The cooling medium like liquid helium held in the cryostat 2, (the pipe 2a and its tip 2b) keeps the pick-up coil 3 in a superconducting state. An exciting magnet (electromagnet) 4 is fitted around the tip 2b in a manner that the exciting magnet 4 may constantly keep an exciting state. The exciting magnet 4 is connected to an exciting control unit 5. The exciting magnet 4 and the pick-up coil 3 (held in the tip 2b) compose a sensor head. This sensor head is moved for scanning on the sample under the control of a driving unit 6.

FIG. 9 is a view showing the sensor head. When the exciting magnet 4 is dc-excited, a dc magnetic field m passes through the sample 1. In this state, the sensor head is moved toward an outlined arrow. During the scan, the dc field m crosses a crack, so that the field may change. The change of the field is sensed by the pick-up coil 3 and then is converted to an electric signal through the effect of the SQUID (not shown).

U.S. Patent application Ser. No. 07/757,585 filed 11 Sep., 1991 now U.S. Pat. No. 5,331,278, which is copending with the present application and has some common inventors, relates to the technical background of the invention of the present application.

SUMMARY OF THE INVENTION

It is an object of the present application to provide a nondestructive inspecting apparatus with a SQUID which has a smaller sensor head and is capable of sensing a small defect like a crack with high accuracy.

The aforementioned prior art is arranged to dc-excite the magnet and sense the change of a field caused when a dc field crosses a crack with the pick-up coil. This arrangement makes it difficult to sense a small crack. To sense a small crack through the effect of a dc magnetic field, it is preferable to keep the arrangement as shown in FIG. 10 and make a magnetic field formed over the sample as uniform as possible. To form the uniform magnetic field, however, it is necessary to keep the exciting magnet 4a at a relatively long distance from the exciting electromagnet 4b and form the core 8 to fit to both of the magnets 4a and 4b. This arrangement results in making the sensor head large, thereby disadvantageously preventing inspection of a narrow spot of the sample.

The object of the present invention is for solving the foregoing disadvantage.

To achieve the object, a nondestructive inspecting apparatus includes a normal conductive exciting magnet for applying a magnetic field to the sample, a pick-up coil for picking up change of a magnetic characteristic of the sample when the magnetic field is applied, and a SQUID for converting the picked change of a magnetic characteristic into an electric signal, the exciting magnet being composed of a cancelled coil assembly composed of plural coils having respective polarities.

According to the foregoing arrangement, the exciting electromagnet is made of the cancelled coil assembly and only the change of a magnetic characteristic based on a defect of the sample is picked up by the pickup coil. Hence, the sensor head is miniaturized. Further, since it is the cancelled coil assembly, the exciting magnet can be dc- or ac-excited. This makes it possible to use various exciting methods for inspecting a defect of the sample.

According to the present invention, since the exciting electromagnet is composed of the cancelled coil assembly, the sensor head can be miniaturized. Further, the exciting magnet can be ac-excited enable sensing of even a small defect with high accuracy.

Moreover, if a single coil is in place of the cancelled coil assembly composed of plural coils, an apparatus for cancelling signal components about an unbalanced ac magnetic field can be provided for sensing even a minute defect with high accuracy.

DESCRIPTION OF THE PREFERRED EMBODIMENTS

Figure 2:
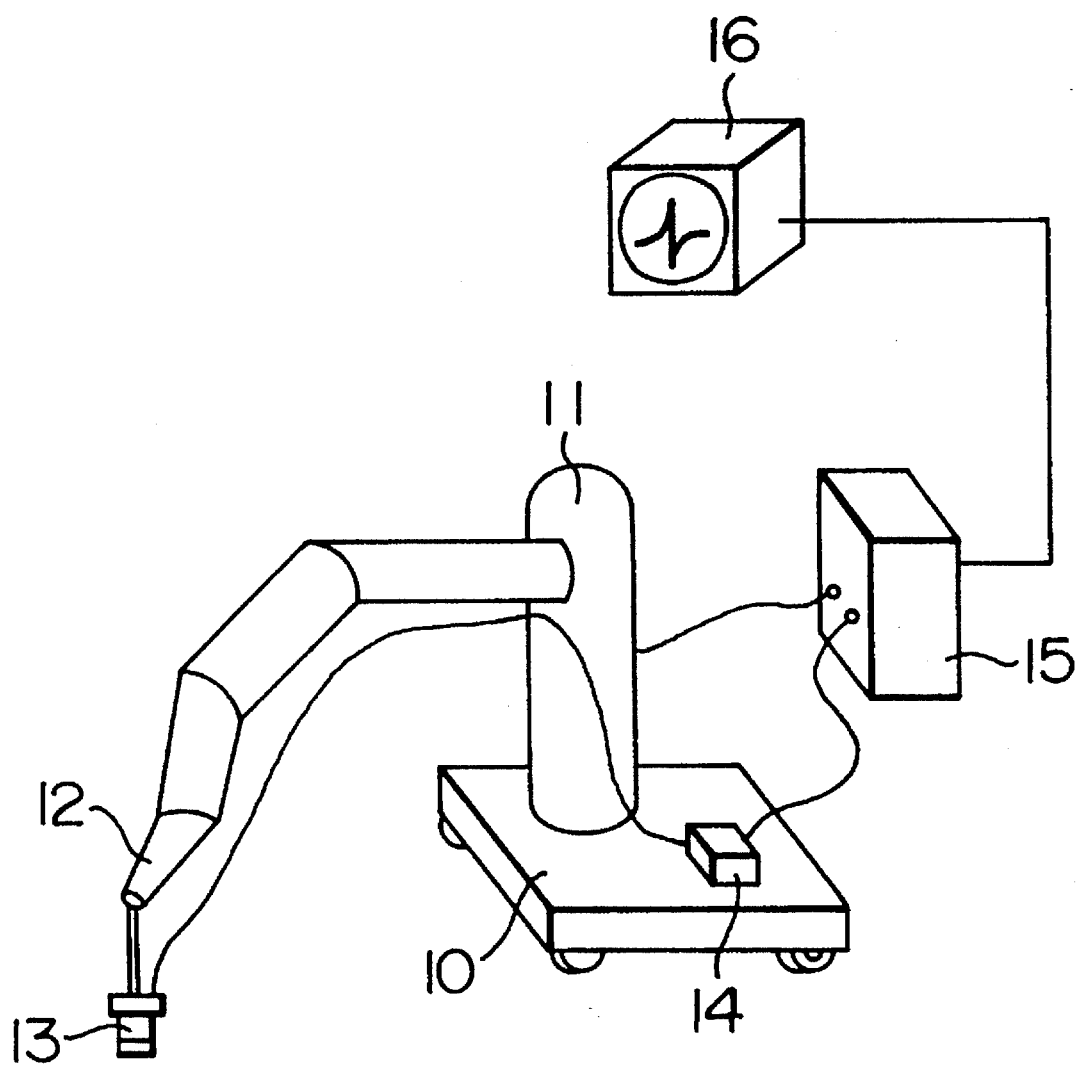
FIG. 2 is a view showing a multi-arm robot having the nondestructive inspecting apparatus shown in FIG.1.

FIG. 2 shows an outer appearance of a nondestructive inspecting apparatus applied to a multi-arm robot. The multi-arm robot 11 provided with a movable cart 10 has a sensor head 13 near a main shaft of a hand tip 12, where noises are relatively small. The sensor head 13 is composed of an exciting magnet and a pick-up coil. The exciting magnet is composed of a cancelled coil assembly (to be discussed later) and a pick-up coil. A cryostat 14 is mounted on the movable cart 10 of the robot 11. Inside of the cryostat 14 is held a SQUID itself which is cooled down to an operating temperature through the effect of a cooling medium such as liquid helium. A control unit 15 operates to control the multi-am robot 11 to move the movable cart 10 to a destination and handle the hand 12 to scan the sensor head 13 on the surface of the sample. The control unit 15 also controls excitation of the SQUID sensor and the magnet so as to display in a display unit 16 the change of a magnetic characteristic on the sample which is picked up by the pick-up coil and converted into an electric signal through the effect of the SQUID itself.

Figure 1:
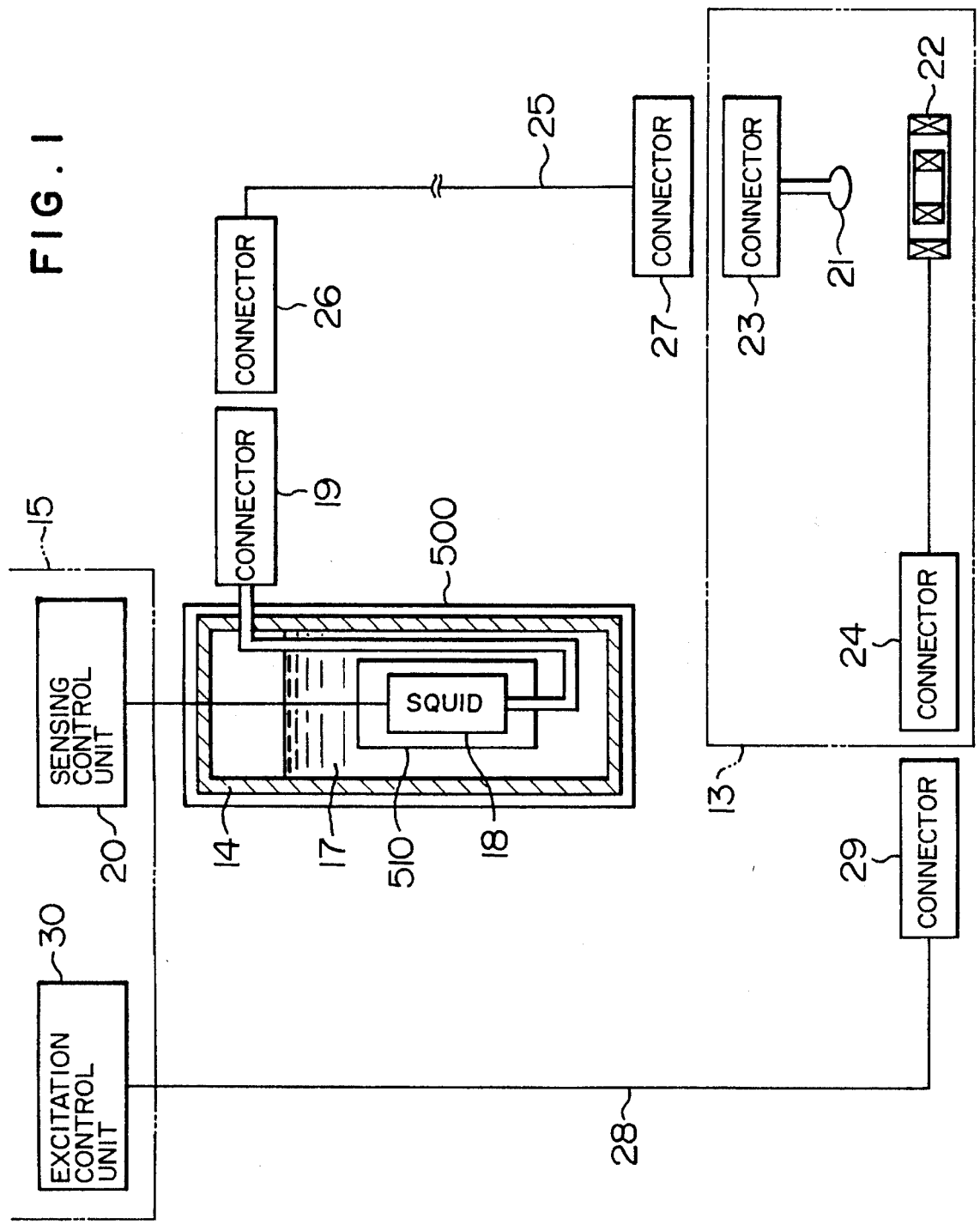
FIG. 1 is a diagram showing an essential part of a nondestructive inspecting apparatus according to an embodiment of the present invention.

FIG. 1 is a diagram showing a connection of the sensor head shown in FIG. 2 with the cryostat 14. Inside of the cryostat 14 magnetically shielded for enhancing noise-proof, liquid helium 17 is held. That is, in the liquid helium 17, the SQUID itself 18 is located. The cryostat 14 has a connector 19 connected to the SQUID 18. The SQUID 18 is connected to a sensing control unit 20 provided in the control unit 15.

The cryostat 14 is required to be made of a nonmagnetic and insulated material so that a magnetic field from the outside may easily pass through the cryostat 14. For example, the preferable material may be fiber-reinforced plastic. As a SQUID element, it is possible to use a low-temperature SQUID made of an NbTi material to be operated at a temperature of liquid helium or a high-temperature SQUID made of YBCO, because the pick-up coil and the ac exciting coil are made of a normal conducting material.

Instead, the pick-up coil and the ac exciting coil may be made of a superconducting material. For this purpose, a system is required for cooling these components.

For enhancing an S/N ratio, it is better to restrict the signal sensed by the SQUID 18 to the signal sensed by the pick-up coil 21. As such, noises from the components except the pick-up coil 21 are required to be shielded. For this purpose, magnetic shields 500 and 510 have to be provided outside of the SQUID 18 or the cryostat 14.

To achieve the necessary magnetic shield, the magnetic shields 500 and 510 are formed by combining a highly permeable material with a low resistive material. In addition, the magnetic shield 500 may be made of a superconducting material for achieving the necessary magnetic shield because the shield 500 may be used in the cooling medium 17. If the cooling medium is liquid helium, an Nb—Ti material may be used for making the shield 500. If it is liquid nitrogen, a YBCO material may be used.

The sensor head 13 mounted to the hand of the robot is composed of a normal conducting pick-up coil 21, an exciting magnet 22 made of a cancelled coil assembly, a connector 23 connected to the pick-up coil 21, and a connector connected to the exciting magnet 22.

To do the nondestructive inspection with this sensor head 13, the sensor head 13 is mounted to the hand 12 of the multi-arm robot 11. One connector 26 provided in a wiring 25 is connected to the connector 19 of the cryostat 14. And, the other connector 27 is connected to the connector 23 of the sensor head 13. Then, the connector 29 of a wiring 28 connected to an excitation control unit 30 of the control unit 15 is connected to the connector of the sensor head 13. As mentioned above, the connecting arrangement uses the connectors. Hence, the replacement of only an element unit such as the sensor head 13 is made easier, thereby enhancing the unit maintenance.

Figure 3:
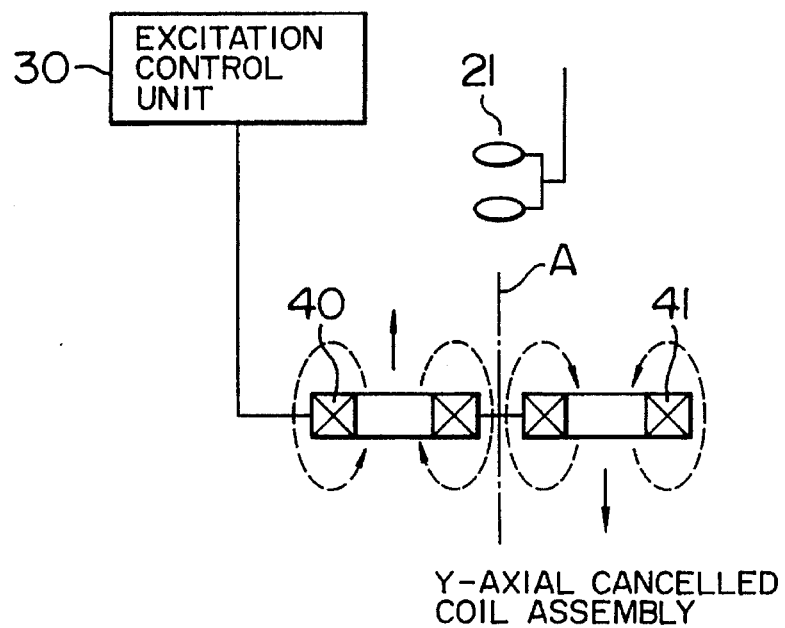
FIG. 3 is an explanatory view showing a Y-axial cancelled coil assembly composed of two coils.

FIG. 3 shows an exciting magnet composed of a Y-axis cancelled coil assembly. According to this embodiment, the exciting magnet is arranged to locate two coils 40 and 41 close to each other on the same level, these coils having their own polarities reverse to each other. When the exciting magnet is dc-excited, if a central magnetic field of the coil 40 is directed upward in FIG. 3, the central magnetic field of the coil 41 is directed downward. The magnetic field exerted between the coils 40 and 41 is cancelled, so that the magnetic field may be made zero around the field-cancelling axis shown in FIG. 3. In the zero field area, the pick-up coil 21 is located. Each of the coils 40 and 41 may have a diameter of about 5 mm. Hence, the sensor head 13 is made smaller.

Figure 4:
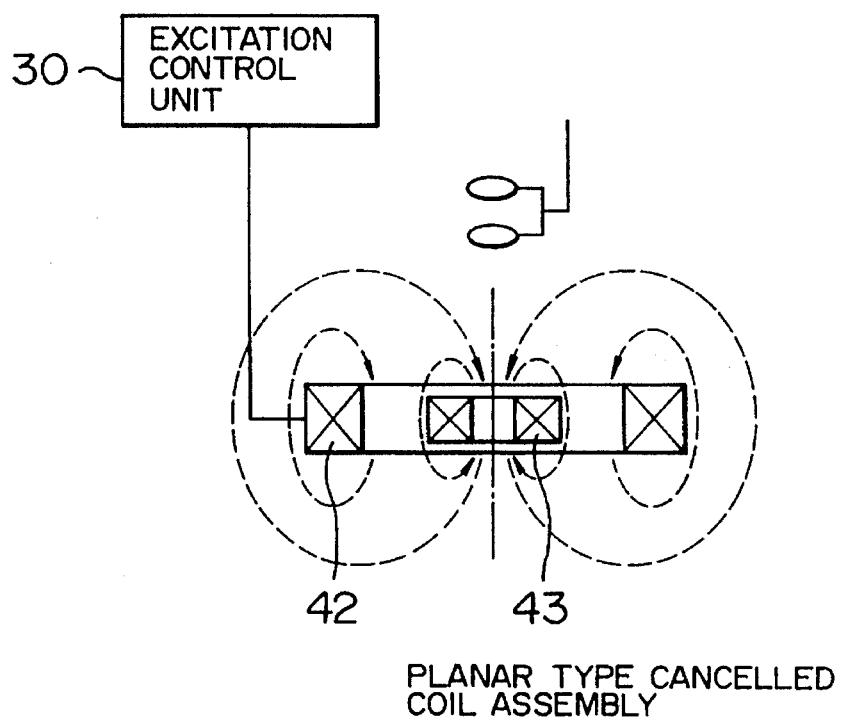
FIG. 4 is an explanatory view showing a planar type cancelled coil assembly composed of two coils.

FIG. 4 shows an exciting electromagnet composed of a planar cancelled coil assembly. According to this embodiment, the exciting electromagnet is made of a coil 42 having a larger diameter and a coil 43 having a smaller diameter, located concentrically inside of the coil 42. When these coils are dc-excited, the magnetic field on the central axis of one coil is reverse to the field on the central axis of the other coil so as to cancel the magnetic fields with each other. Then, the pick-up coil 21 is located in the area where the synthesized magnetic field is made zero.

Figure 5:
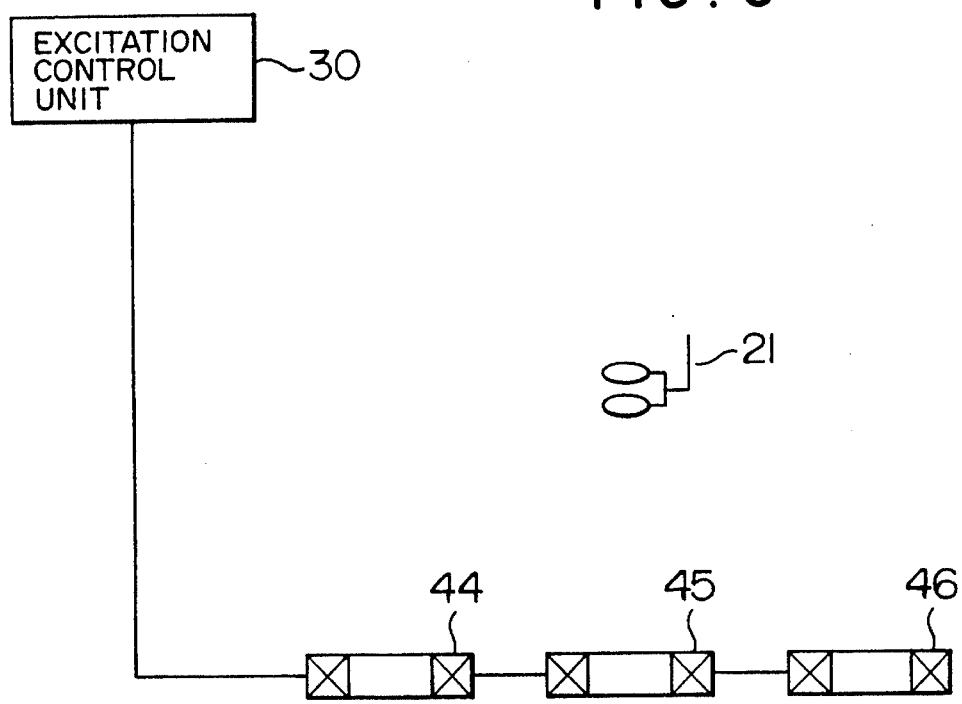
FIG. 5 is an explanatory view showing a Y-axial cancelled coil assembly composed of three coils.
Figure 6:
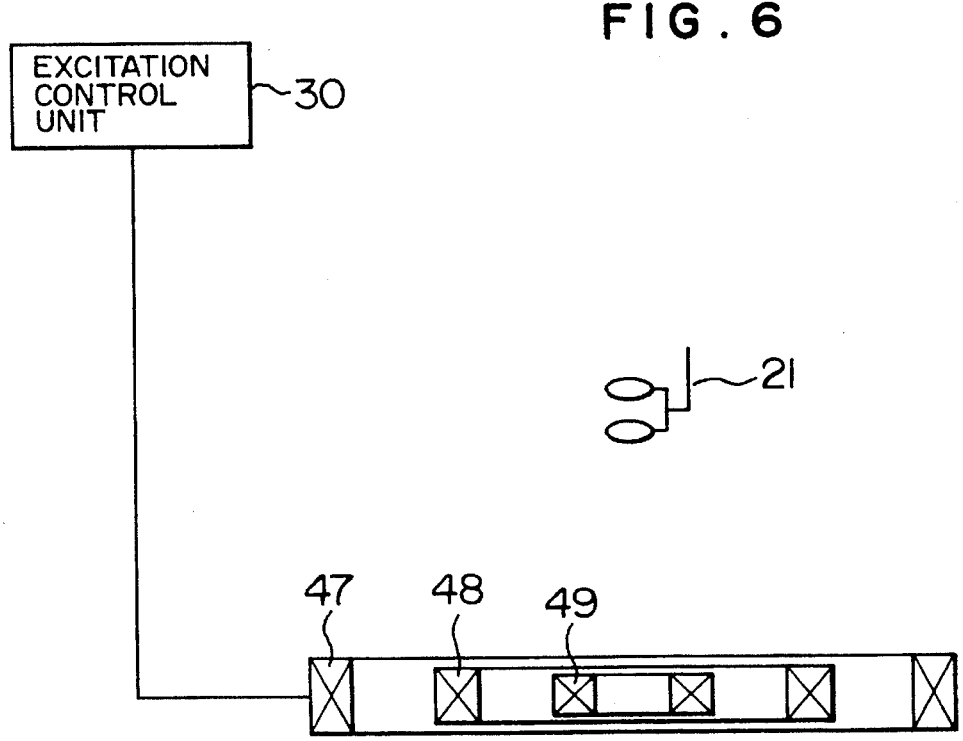
FIG. 6 is an explanatory view showing a planar type cancelled coil assembly composed of three coils.

FIGS. 3 and 4 show an exciting magnet composed of two coils having reverse polarities to each other. However, it goes without saying that three or more coils may be used for composing the electromagnet. In FIG. 5, three coils 44, 45, 46 are located in parallel and on the same level so that the pick-up coil 21 may be placed on the central axis of the middle coil 45. The polarity (direction of the winding) and the number of the windings of each of the coils 44, 45 and 46 are defined so that when the same magnitude of current flows through each of these coils, the magnetic fields generated in the coils may be cancelled to zero on the central axis of the coil 45. FIG. 6 shows the cancelled coil assembly composed of three coils 47, 48 and 49 located concentrically. The polarity and the number of winds of each coil are defined so that the synthesized magnetic field on the central axis of the middle coil where the pick-up coil 21 is located.

Figure 7A:
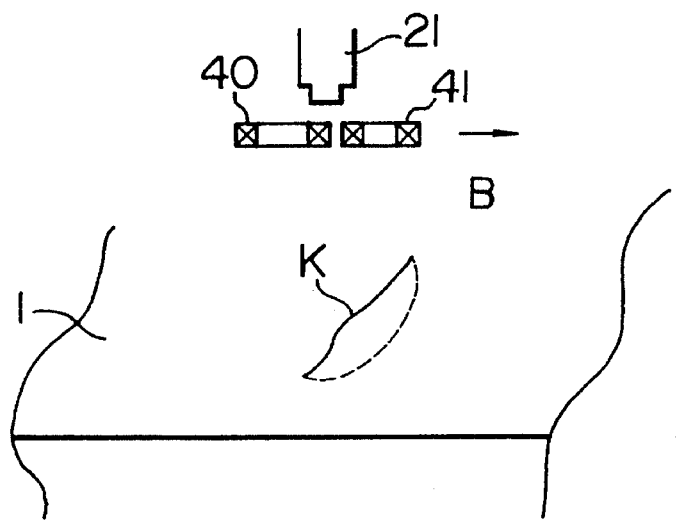
FIG. 7A is a view showing an example of a sensed signal.
Figure 7B:
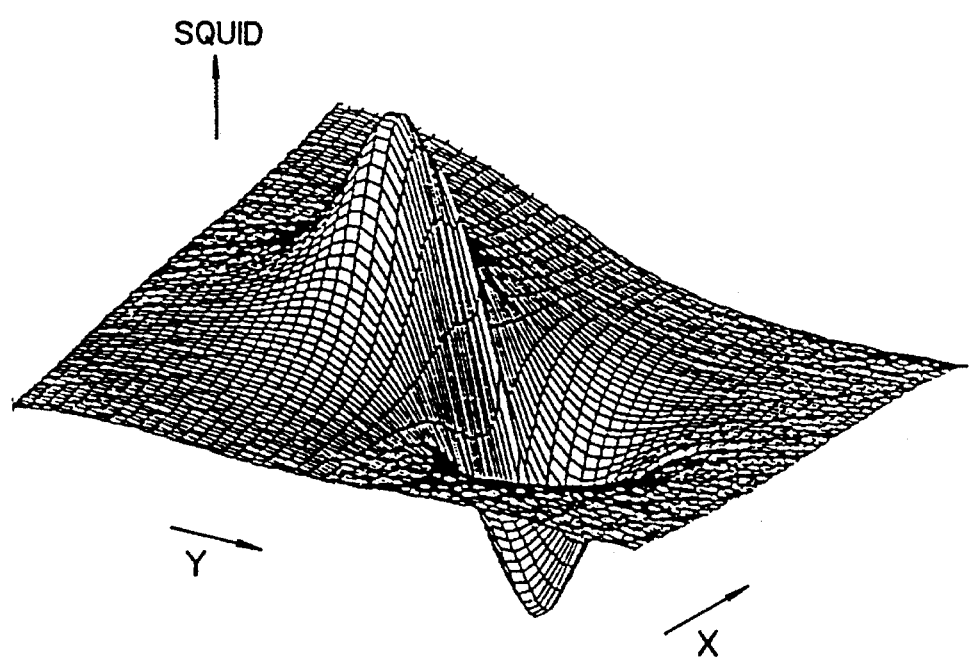
FIG. 7B is a view showing an example of representation of the sensed signal.

To check the pipes provided in the nuclear power plant for defects with the nondestructive inspecting apparatus arranged as described above, the robot 11 is traveled to the pipe to be checked. Then, the hand 12 is controlled to operate so that the sensor head 13 may scan along the surface of the pipe. As shown in FIG. 7A, the cancelled coil assemblies 40 and 41, may be ac excited and the ac magnetic field generated therein inside of the sample 1 so as to magnetize the part of the pipe where the magnetic field is applied. With the scan of the sensor head 13, the ac magnetic field moves toward the arrow B and crosses a crack K. Before and after crossing the crack K, the magnetic characteristic of the magnetized part of the sample 1 is reversed. Though the ac magnetic field is constantly balanced to zero in the area where the pick-up coil 21 is located, the magnetic field generated by the reverse of the magnetic characteristic is sensed by the differential type pick-up coil 21 and then is converted into an electric signal through the effect of the SQUID. The converted signal is displayed in the display unit 16 (see FIG. 2). The signal waveform obtained by two-dimensionally doing this scan on the surface of the sample 1 may be represented three-dimensionally as shown in FIG. 7B. The signal waveform shown in FIG. 7B is a three-dimensional representation of a differential waveform itself in which the magnetic characteristic is reversed. In actual, the form of the crack may be derived from the signal waveform and then be displayed on the screen. Further, instead of the ac excitation of the magnets, it goes without saying that the magnets may be dc-excited.

Figure 8:
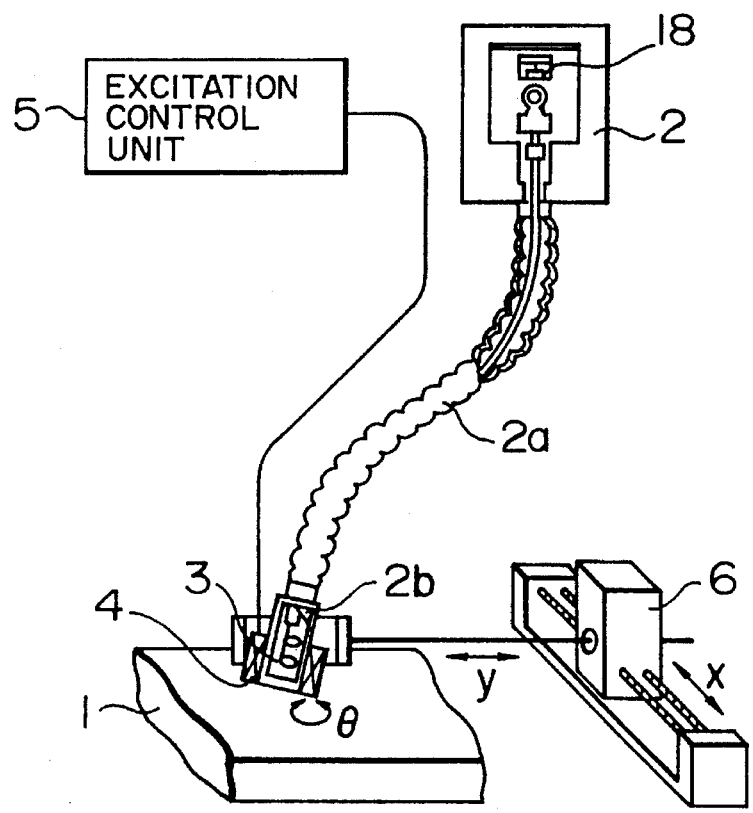
FIG. 8 is a diagram showing a conventional nondestructive inspecting apparatus.
Figure 9:
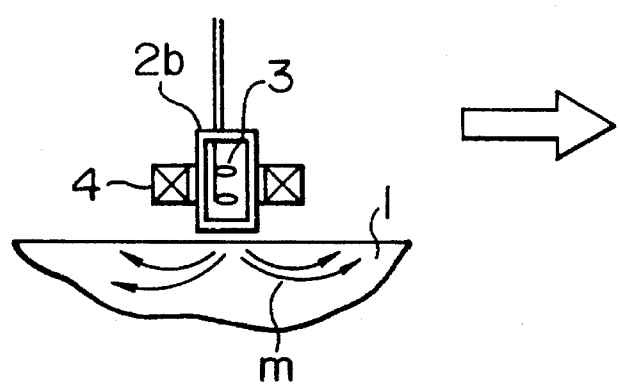
FIG. 9 is a diagram showing a sensor head as shown in FIG. 8.
Figure 10:
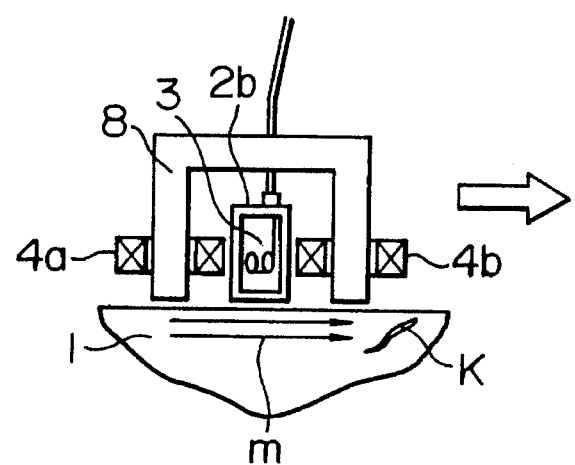
FIG. 10 is a diagram showing another conventional nondestructive inspecting apparatus.

In the foregoing embodiments, the normal conducting pick-up coil 21 is used. In place, a superconducting pick-up coil may be used as well. In this case, however, the pick-up coil is also required to be cooled down to a low temperature through the effect of the cooling medium. Like the foregoing prior art (see FIG. 8) disclosed in J-P-A-2-78983, therefore, the cryostat is formed to have a flexible pipe so that the part may be extended. At the tip of the pipe, the pickup coil is held. The pick-up coil is excited by the exciting magnet composed of the cancelled coil assembly and an excitation control means for exciting the exciting electromagnet by dc or ac having a specific waveform for the purpose of inspecting the sample.

As another way of cancelling the magnetic field based on the ac excitation, an electric signal is allowed to be fed back to the SQUID for keeping the same performance.

Figure 11:
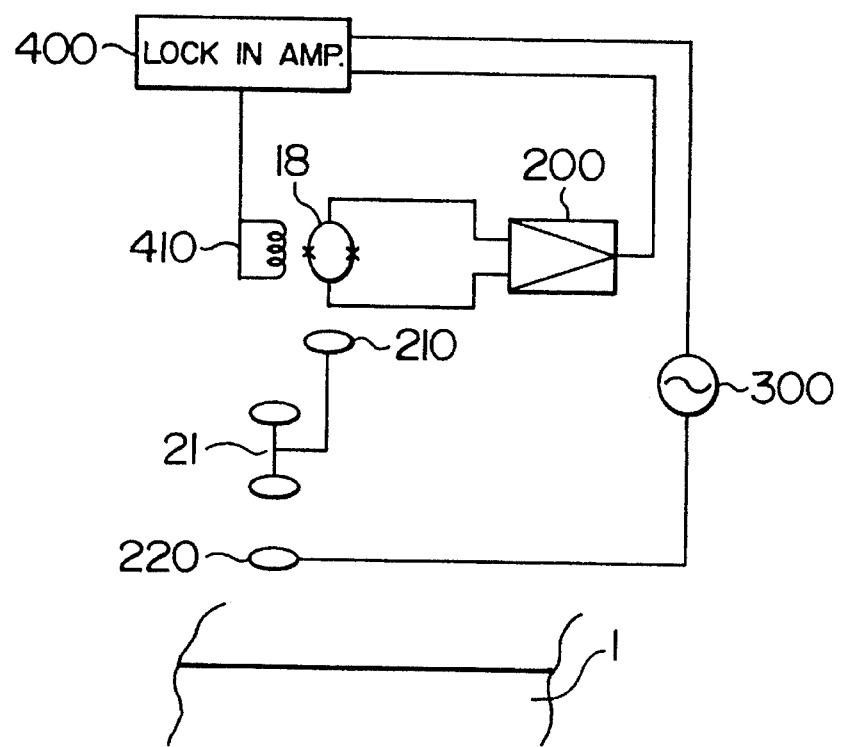
FIG. 11 is a block diagram showing a nondestructive inspecting apparatus using an electric feedback method according to another embodiment of the present invention.

FIG. 11 shows the arrangement based on the electric feedback system according to an embodiment of the invention. A numeral 229 denotes a single polarity coil or a cancelled coil assembly. A numeral 300 denotes an ac-exciting power source. A numeral 210 denotes an input coil for coupling the magnetic field sensed by the pick-up coil 21 to the SQUID 18. A numeral 200 denotes a controller for the SQUID. The signal of the ac-exciting power source 300 and the output of the SQUID controller 200 are applied to a lock-in amplifier 400.

Figure 12:
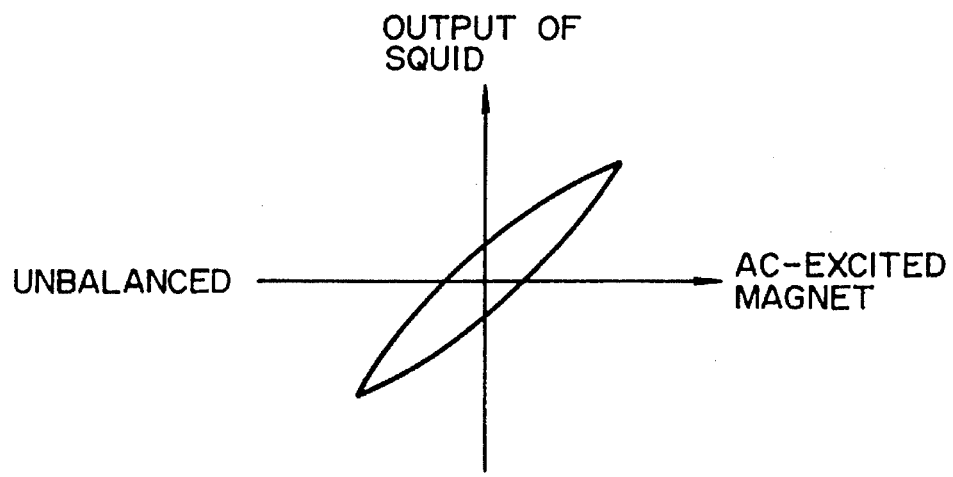
FIG. 12 is a graph showing an initial unbalanced state of the nondestructive inspecting apparatus.
Figure 13:
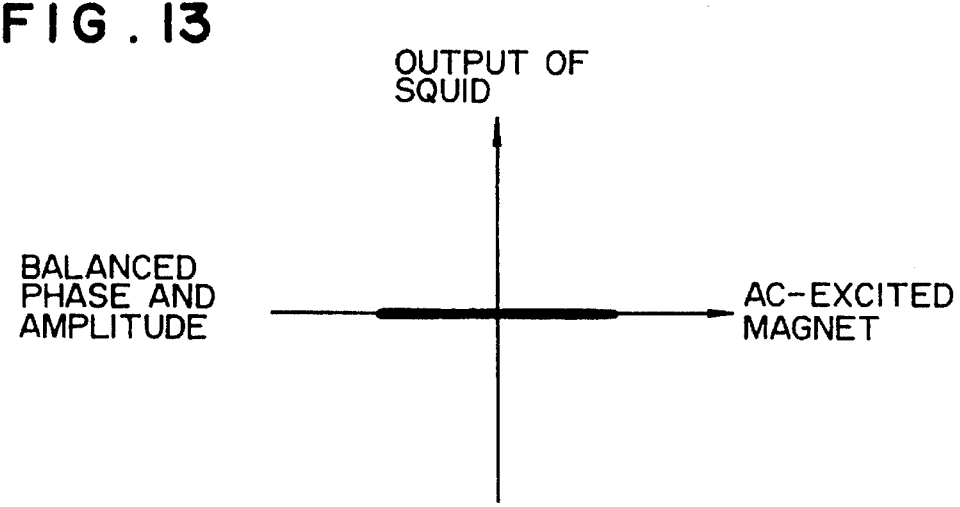
FIG. 13 is a graph showing a state where an output of a SQUID controller 200 is adjusted to zero by applying a signal of a reverse phase amplitude against an output of the SQUID controller 200, based on the reference signal of an ac-exciting power source 300, to a feedback coil 410 through the effect of a lock-in amplifier 400.
Figure 14:
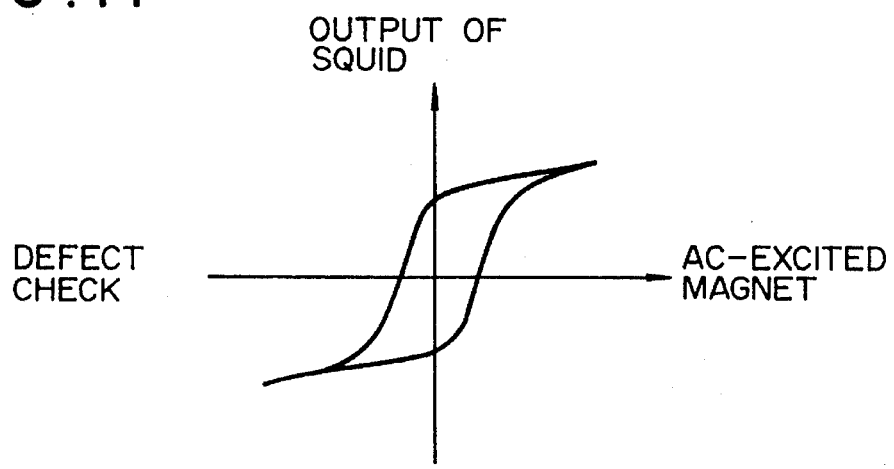
FIG. 14 is a graph showing a signal state in which the head is moved to a spot to be checked after balanced.

FIGS. 12 to 14 shows the operation of the embodiment shown in FIG. 11.

FIG. 12 shows an initial unbalanced state. If no defect is actually found out, a hysteresis curve against the magnetic field based on the ac excitation appears because of the unbalance between the magnetic characteristics of the material or the excitation coil and the pick-up coil. The hysteresis curve corresponds to the noises mingled in the output of the SQUID. To cope with the hysteresis curve, the signal having a reverse phase amplitude to the output of the SQUID controller 200 based on the reference signal of the ac-exciting power source 300 is applied to a feedback coil 410 through the effect of the lock-in amplifier 400 so as to adjust the output of the SQUID controller 200 to be zero. The adjusted state is shown in FIG. 13. Then, the sensor head is moved to the part to be checked for obtaining a signal. The sensed state is as shown in FIG. 14.

Figure 15:
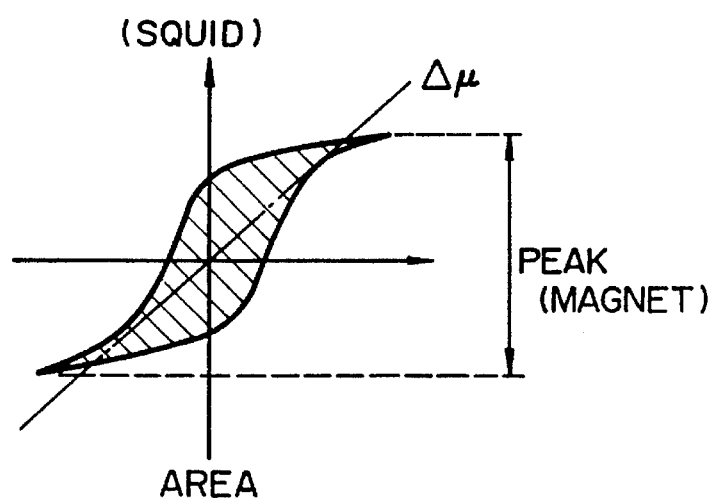
FIG. 15 is a graph showing a state in which some parameters such as an inclination against permeability change, a hysteresis loop area S and a maximum amplitude P-P are derived with respect to the sensed signal.
Figure 16:
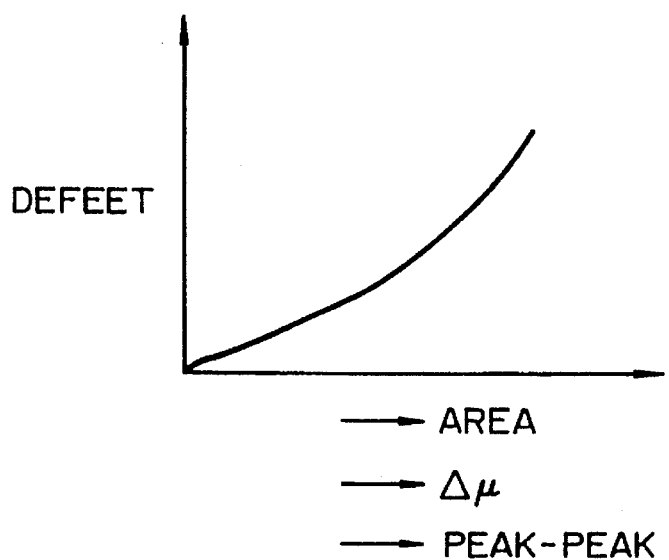
FIG. 16 is a graph showing a master curve derived from a reference sample.

The signal obtained with this method is derived from only a magnetic characteristic of the checked part or a difference between the magnetic characteristic of the defective part and that of the normal part. Hence, the sample may be checked with high accuracy. For example, some parameters such as an inclination against a change of permeability, a hysteresis loop area S and a maximum amplitude P-P are derived with respect to the sensed signal as shown in FIG. 15. Then, the defect of the part to be checked is estimated along the master curve as shown in FIG. 16 which is derived from a reference sample.

According to this embodiment, it is electrically easy to cancel the unbalance of the exciting coil or the SQUID sensor system and possible to keep the functions if an ac-exciting coil is exchanged, thereby being able to obtain the multiplicity.

What is claimed is:

1. A nondestructive inspecting apparatus with a SQUID comprising:

an exciting magnet having a cancelled coil assembly composed of plural coils, for applying a magnetic field to a sample, said plural coils having individual polarities and being disposed so that a magnetic field extending in a direction at least one of along and substantially parallel to an axial direction of said plural coils is cancelled;

a pick-up coil for sensing change of a magnetic characteristic of said sample when said exciting magnet applies the magnetic field to said sample, said pick-up coil being located so that an axis thereof extends one of along and substantially parallel to the direction in which the magnetic field is cancelled by said plural coils of said cancelled coil assembly;

a SQUID for converting the change of a magnetic characteristic sensed by said pick-up coil into an electric signal.

2. A nondestructive inspecting apparatus as claimed in claim 1 further comprising means for ac exciting said exciting magnet.

3. A nondestructive inspecting apparatus as claimed in claim 1, wherein said pick-up coil is located in an area in which a magnetic field is cancelled by said plural coils.

4. A nondestructive inspecting apparatus as claimed in claim 1, wherein said pick-up coil is a superconducting coil and composes a sensor head together with said exciting magnet, said sensor head being separate from said SQUID, and further comprising a cryostat for holding a cooling medium for cooling said SQUID down to an operating temperature, part of said cryostat being an extensible flexible pipe, and said flexible pipe having said pick-up coil in the tip thereof.

5. A nondestructive inspecting apparatus as claimed in claim 4, further comprising a scanning unit for scanning said sensor head against said sample.

6. A nondestructive inspecting apparatus as claimed in claim 4, wherein said sensor head is mounted to the hand of a multi-arm robot.

7. A nondestructive inspecting apparatus as claimed in claim 1, wherein said plural coils are arranged in a same plane so as to be one of spaced from one another with different axes and concentrically arranged about the same axis.

8. A nondestructive inspecting apparatus comprising:

an exciting magnet having a cancelled coil assembly composed of plural coils, for applying a magnetic field to a sample, said plural coils having individual polarities and being disposed so that a magnetic field extending in a direction at least one of along and substantially parallel to an axial direction of said plural coils is cancelled;

exciting control means being connected to said exciting magnet through a connector and for controlling said magnetic field;

a pick-up coil for sensing change of a magnetic characteristic occurring on said sample when said exciting magnet applies the magnetic field onto said sample, said pick-up coil being located so that an axis thereof extends one of along and substantially parallel to the direction in which the magnetic field is cancelled by said plural coils of said cancelled coil assembly;

a SQUID being connected to said pick-up coil through a connector, for converting the change of a magnetic characteristic sensed by said pick-up coil into an electric signal;

a cooling medium for cooling said SQUID down to an operating temperature;

a cryostat having said cooling medium;

shielding means for magnetically shielding at least one of said SQUID and said cryostat; and a sensor head being provided separately from said exciting control means and said SQUID and having said exciting magnet and said pick-up coil built therein.

9. A nondestructive inspecting apparatus as claimed in claim 8, wherein said plural coils are arranged in a same plane so as to be one of spaced from one another with different axes and concentrically arranged about the same axis.

10. A nondestructive inspecting apparatus comprising:

an ac power source;

an exciting magnet having a cancelled coil assembly composed of plural coils being connected to said ac power source, for applying an ac magnetic field to a sample, said plural coils having individual polarities and being disposed so that a magnetic field extending in a direction at least one of along and substantially parallel to an axial direction of said plural coils is cancelled;

a pick-up coil for sensing change of a magnetic characteristic of said sample when said exciting magnet applies the ac magnetic field to said sample, said pick-up coil being located so that an axis thereof extends one of along and substantially parallel to the direction in which the magnetic field is cancelled by said plural coils of said cancelled coil assembly;

a SQUID for converting the change of a magnetic characteristic sensed by said pick-up coil into an electric signal; and means for cancelling signal components about an initial unbalanced ac-exciting magnetic field contained in said electrical signal.

11. A nondestructive inspecting apparatus as claimed in claim 10, wherein said cancelling means includes a circuit for applying a feedback of a reverse phase and amplitude with respect to a signal from said ac power source to said pick-up coil so as to set the output of said SQUID zero at a reference location.

12. A nondestructive inspecting apparatus as claimed in claim 10, wherein said plural coils are arranged in a same plane so as to be one of spaced from one another with different axes and concentrically arranged about the same axis.

* * * * *